(12) United States Patent
Camblong et al.

(10) Patent No.: US 10,952,953 B2
(45) Date of Patent: Mar. 23, 2021

(54) SKIN CLEANSING COMPOSITION

(71) Applicant: L'OREAL, Paris (FR)

(72) Inventors: Emmanuelle Camblong, Gigors-et-Lozeron (FR); Céline Marcq, Gigors-et-Lozeron (FR); Valérie Page, Gigors-et-Lozeron (FR)

(73) Assignee: L'OREAL, Paris (FR)

( * ) Notice: Subject to any disclaimer, the term of this patent is extended or adjusted under 35 U.S.C. 154(b) by 141 days.

(21) Appl. No.: 16/065,447

(22) PCT Filed: Dec. 20, 2016

(86) PCT No.: PCT/EP2016/081946
§ 371 (c)(1),
(2) Date: Jun. 22, 2018

(87) PCT Pub. No.: WO2017/108807
PCT Pub. Date: Jun. 29, 2017

(65) Prior Publication Data
US 2019/0021978 A1    Jan. 24, 2019

(30) Foreign Application Priority Data

Dec. 24, 2015 (FR) ..................................... 1563339

(51) Int. Cl.
| | | |
|---|---|---|
| *A61K 36/886* | (2006.01) | |
| *A61K 36/00* | (2006.01) | |
| *A61K 8/73* | (2006.01) | |
| *A61K 8/34* | (2006.01) | |
| *A61Q 19/10* | (2006.01) | |
| *A61K 8/04* | (2006.01) | |
| *A61K 8/02* | (2006.01) | |
| *A61Q 1/14* | (2006.01) | |
| *A61K 8/92* | (2006.01) | |
| *A61K 8/9794* | (2017.01) | |

(52) U.S. Cl.
CPC ............ *A61K 8/732* (2013.01); *A61K 8/0212* (2013.01); *A61K 8/042* (2013.01); *A61K 8/34* (2013.01); *A61K 8/92* (2013.01); *A61K 8/9794* (2017.08); *A61Q 1/14* (2013.01); *A61Q 19/10* (2013.01)

(58) Field of Classification Search
None
See application file for complete search history.

(56) References Cited

FOREIGN PATENT DOCUMENTS

| | | |
|---|---|---|
| FR | 2964035 A1 | 2/2012 |
| FR | 3007645 | 1/2015 |
| WO | WO2012052536 A2 * | 4/2012 |
| WO | 2014128679 A1 | 8/2014 |
| WO | 2015019323 A1 | 2/2015 |

OTHER PUBLICATIONS

FR 3 007 645 A1 (Oreal [FR]) Jan. 2, 2015 (Jan. 2, 2015, in IDS, pp. 1-10) (Year: 2015).*
International Search Report PCT/EP2016/081946.

* cited by examiner

*Primary Examiner* — Michael Barker
*Assistant Examiner* — Randall O Winston
(74) *Attorney, Agent, or Firm* — McNees Wallace & Nurick LLC

(57) ABSTRACT

The present invention relates to a composition of aqueous gel type comprising from 7.5% to 13.5% by dry weight, relative to its total weight, of at least one modified cross-linked $C_1$-$C_4$ carboxyalkyl starch and at least one $C_2$-$C_5$ monoalcohol. A composition according to the invention is in particular of use as a skin cleansing mask, in particular a face cleansing mask. The invention also relates to a process for the preparation thereof, to a process for cosmetic treatment of keratin materials and to a cosmetic process for cleansing a keratin material.

17 Claims, 1 Drawing Sheet

SKIN CLEANSING COMPOSITION

The present invention relates to the field of keratin material care compositions, more particularly that of skin cleansing compositions and in particular facial skin cleansing masks.

Beauty mask products are well known in the cosmetics field. These beauty masks are constituted of films which form upon application to the treated skin and which, after drying with a certain leave-on time, are removed by rinsing or by peeling, i.e. by pulling off or by pilling while forming more or less large pills, in particular masks based on synthetic polymers such as polyvinylpyrrolidone or polyvinyl alcohol or natural polymers, for instance alginates linked to calcium ions.

They may be in gel, emulsion or paste form. Various formulations of this mask type are thus described in the literature, for example in "Cosmetic and Toiletry Formulations", Second edition, Ernest W. Flick 1992. However, the galenical form preferred for the production of cleansing mask compositions is generally a galenical form of aqueous gel type.

Indeed, this aqueous gel galenical form provides a light feel on application and during the leave-on time. In addition, it has the advantage of providing a transparent/translucent visual appearance and a feeling of freshness on application, two effects which users find particularly pleasant. It also proves to be easy to remove after use, since rinsing with water can be sufficient.

Unfortunately, the majority of aqueous gel galenical forms also generate a dragging effect on application and provide a coarse and tacky skin finish combined with a lack of softness. In addition, their appearance is generally perceived as "viscous and slimy" and they feel runny when taken up. In order to overcome these negative aspects, it is usual to formulate these aqueous gels with a fatty liquid phase which unfortunately needs to be combined with at least one emulsifier. However, the addition of an emulsifier very often leads to loss of the transparent/translucent appearance (opacification) and can generate discomfort, in particular in the context of a mask application (i.e. application in a thick layer with a long leave-on-time). It also changes the sensory perception of the aqueous gel and thus contributes to a loss of feeling of lightness and freshness.

There thus remains a need for beauty mask products free of the abovementioned drawbacks.

Moreover, there is an expectation for products which have an improved environmental profile, in particular by proposing novel galenical forms that are alternatives to the polyethylene beads conventionally considered in products of this type for providing more efficient skin cleansing.

Finally, there is at the current time a clear attraction for the consumers, for cosmetic products which are termed "natural" because they use, as essential constituents, ingredients that are natural, of natural origin and/or "certified organic".

Consequently, users are searching for products which simultaneously meet their expectations in terms of cosmeticity and sensoriality, which have less of an environmental impact, and which preferably favor ingredients which are natural, of natural origin and/or certified organic.

The object of the present invention is precisely to meet these expectations.

Thus, the present invention is directed toward, in the main, a composition, especially a cosmetic composition, which is in particular a skin care and/or cleansing composition, and more particularly of skin cleansing mask type, said composition being of aqueous gel type, and comprising from 7.5% to 13.5% by dry weight of at least one crosslinked $C_1$-$C_4$ carboxyalkyl starch relative to its total weight and at least one $C_2$-$C_5$ monoalcohol.

Advantageously, the composition is a single-phase composition.

More specifically, the inventors have noted that the combination, in an aqueous medium, of a gelling system formed from at least one crosslinked modified starch and of a $C_2$-$C_5$ lower alcohol, and in particular of ethanol, makes it possible to obtain an aqueous gel that is particularly advantageous for forming a cleansing mask having the expected sensory properties while at the same time not requiring the presence of fatty substances and preferably containing less than 0.5% by weight of surfactants, the presence of which can induce adverse effects.

The gelling system under consideration according to the invention thus makes it possible to obtain gels of various viscosities, ranging from a care galenical form to the thicker one of a mask.

By way of representation of the modified crosslinked starches suitable for the invention, mention may be most particularly made of those which derive from starches obtained from the potato tuber.

It may also be a crosslinked sodium carboxymethyl starch [INCI "sodium carboxymethyl starch"], for instance sold under the trade reference "Glycolys" by Roquette.

Products of this type are, to the inventors' knowledge, essentially exploited in industrial fields very different from the cosmetics field, such as the food and pharmaceutical fields, where they are used as excipients for improving the solublization and bioavailability of a drug or of any other compound, that is to say a function totally different from that under consideration according to the invention.

The inventors have also noted that the use thereof in a form combined with ethanol unexpectedly makes it possible to obtain an immediate fresh effect potentiated by the structure of the gelling agent.

Consequently, a composition according to the invention, in particular of cleansing mask type, is advantageous in several respects.

First of all, and as emerges from the explanations hereinafter, they provide the sensory and effectiveness properties expected.

More specifically, they exhibit a flexible, uniform, translucent, matte appearance, with a slight "grained" appearance.

For the purposes of the invention, the term "flexible" characterizes the fact that the composition is capable of deforming when taken up with the fingers and is easy to grasp.

For the purposes of the invention, the term "uniform" means that the composition is formed from a single phase with an identical structure in all respects.

For the purposes of the invention, the term "matte" means non-shiny.

For the purposes of the invention, the term "translucent" means that the composition according to the invention allows light to partially pass through it without however making it possible to clearly distinguish an object on the other side.

For the purposes of the invention, the term "grained" characterizes an appearance which has a slight granular, icy-frosty effect.

They are stable over time and at a temperature ranging from 4° C. to 55° C.

As soon as they are applied, they provide particularly beneficial sensory perceptions, such as freshness and glidance.

Finally, as emerges from the examples hereinafter, they can be easily removed after use, by simple rinsing or by pilling with a gentle exfoliating action.

They thus provide effective skin cleansing while at same time being gentle and this results in a soft, non-tacky skin finish.

Moreover, as opposed to cleansing compositions based on polyethylene beads, the compositions according to the invention have a significantly reduced environmental impact.

Finally, they can essentially be composed of ingredients that are natural or of natural origin.

For the purposes of the invention, the natural raw materials are derived from the plant, mineral or marine world (for example algae) category or beehive products and are understood to be non-transformed or physically transformed. The raw materials of natural origin are derived from the same categories and are understood to be chemically transformed, preferentially according to the principles of green chemistry, i.e. with as little environmental impact as possible (see Anastas P., Warner J. C., Green Chemistry, Oxford University Press, New York, 1998, p. 30).

The present invention is also directed toward a process for preparing said composition, comprising at least the steps consisting in providing a homogeneous aqueous dispersion of at least 7.5% by dry weight of at least one modified crosslinked $C_1$-$C_4$ carboxyalkyl starch relative to the total weight of said aqueous dispersion and bringing this aqueous dispersion into contact with at least one $C_2$-$C_5$ lower alcohol.

It is also directed toward a process for the cosmetic treatment of keratin materials such as the skin, in which a composition as defined according to the invention is applied to said keratin materials, and in particular the skin.

As emerges from the aforementioned, a composition according to the invention is advantageously in the form of a skin cleansing composition and preferably a skin cleansing mask, more particularly a face cleansing mask.

It is also directed toward a cosmetic process for cleansing a keratin material, in particular the skin and more particularly facial skin, comprising at least the steps consisting in:
forming, at the surface of said keratin material to be treated, a mask from a composition according to the invention, and
removing said mask by rinsing and/or by pilling.

DETAILED DESCRIPTION

The composition according to the invention is advantageously cosmetic.

The term "cosmetic composition" is intended to mean a substance or a preparation intended to be brought into contact with the various superficial parts of the human body, in particular the epidermis, the lips and the oral mucous membranes, with a view, exclusively or mainly, to cleansing them, making them more attractive, fragrancing them, modifying their appearance, protecting them, keeping them in good condition, or correcting body odors.

The composition according to the invention may comprise a "physiologically acceptable medium".

For the purposes of the present invention, the term "physiologically acceptable medium" is intended to mean a medium that is suitable for the topical administration of a composition, and that is compatible with all human keratin materials, such as the skin, the lips, the nails, the mucous membranes, the eyelashes, the eyebrows, the scalp and/or the hair, or any other area of bodily skin. According to the invention, a physiologically acceptable medium is preferentially a cosmetically acceptable medium, that is to say a medium which is free of any odor or unpleasant appearance and which is entirely compatible with the topical administration route.

As mentioned above, the compositions according to the invention have a viscosity suitable, on the one hand, for being taken up with the fingers and for uniform spreading on the skin by the user at the time of application and, on the other hand, for a wear property on the skin during the leave-on time without undesirable running.

This viscosity is advantageously at least equal to 20 Pa·s, and preferably greater than 100 Pa·s, for a shear rate of 1 s$^{-1}$.

A composition according to the invention also has a certain elasticity. This elasticity may be characterized by a complex modulus G* which, under this minimum stress threshold, is at least equal to 500 Pa and preferably greater than 3000 Pa. The value G* of a composition may be obtained by subjecting the composition under consideration to a strain of 0.1% in the linear regime and for a set frequency of 1 Hz.

These values in Pas are determined by oscillation and obtained at 25° C. using a Haake Mars II imposed-stress rheometer equipped with a plate-cone measuring body (diameter 60 mm, 1 degree and in sanded titanium, 25° C.). For each measurement, the sample is carefully put in place and the gap is set at 0.052 mm.

The compositions according to the invention are also characterized by a viscosity between 50 DU and 150 DU.

This measurement is carried out by means of a rheometer (Rheomat RM200 from Lamy) using spindle 4. The viscosity is taken at D1, then T2M at ambient temperature and at 45° C. The measurement is thermostated at 25° C.

Crosslinked ($C_1$-$C_4$) Carboxyalkyl Starches

A composition according to the invention comprises from 7.5% to 13.5% by dry weight, advantageously from 7.5% to 12% by dry weight and preferably from 9% to 12% by dry weight of at least one modified crosslinked starch in accordance with the invention, relative to its total weight.

Indeed, as emerges from the examples hereinafter, too small an amount of modified crosslinked starch does not make it possible to obtain a gel structure that is stabilized over a sufficient period of time.

Likewise, too high a proportion of modified crosslinked starch results in a formulation that is not sufficiently satisfactory in terms of handling since it is too thick and thus more difficult to spread uniformly on the skin. This consistency is not that expected for an aqueous gel according to the invention.

The starch derivatives used in the present invention may originate from a plant source such as cereals, tubers, roots, vegetables and fruit.

Thus, the starch(es) may originate from a plant source chosen from corn, pea, potato, sweet potato, banana, barley, wheat, rice, oat, sago, tapioca and sorghum. The starch is preferably derived from potato.

Starches are generally in the form of a white powder, which is insoluble in cold water, whose elemental particle size ranges from 15 to 100 microns.

In the context of the present invention, these starches are used in a form that has been crosslinked and in a form that has been chemically modified by functionalization with carboxyalkyl units.

The aim of the crosslinking is to form a network that is much more stable to heat and more resistant to heat and to acidity. The starch chains are linked to one another by bonding molecules: phosphated derivatives, chloroepoxide derivatives, acid dianhydrides and aldehyde derivatives.

The ($C_1$-$C_4$) carboxyalkyl starches, also referred to hereinafter as "carboxyalkyl starches", are obtained by grafting carboxyalkyl groups onto one or more alcohol functions of starch, in particular by reaction of starch and of sodium monochloroacetate in alkaline medium.

The carboxyalkyl groups are generally attached via an ether function, more particularly to carbon 1.

The degree of substitution with carboxyalkyl units of the $C_1$-$C_4$ carboxyalkyl starch preferably ranges from 0.1 to 1 and more particularly from 0.15 to 0.5. The degree of substitution is defined according to the present invention as being the mean number of hydroxyl groups substituted with an ester or ether group per monosaccharide unit of the polysaccharide.

The carboxyalkyl starches are advantageously used in the form of salts and especially of salts of alkali metals or alkaline-earth metals such as Na, K, Li, $NH_4$, or salts of a quaternary ammonium or of an organic amine such as monoethanolamine, diethanolamine or triethanolamine.

The $C_1$-$C_4$ carboxyalkyl starches are advantageously, in the context of the present invention, carboxymethyl starches.

The carboxymethyl starches preferably comprise units having the following formula:

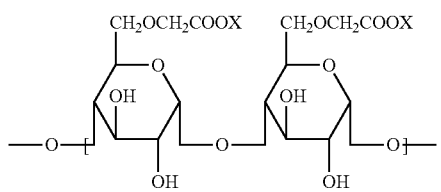

in which X, covalently or non-covalently bonded to the carboxylic unit, denotes a hydrogen atom, an alkali metal or alkaline-earth metal such as Na, K, Li, $NH_4$, a quaternary ammonium or an organic amine, for instance monoethanolamine, diethanolamine or triethanolamine.

Preferably, X Denotes an Na+ Cation.

The carboxyalkyl starches that may be used according to the present invention are partially or totally crosslinked carboxyalkyl starches.

In general, a crosslinked carboxyalkyl starch has, in contrast with a non-crosslinked carboxyalkyl starch, an increased, controllable viscosity of increased stability. The crosslinking thus makes it possible to reduce the syneresis phenomena and to increase the resistance of the gel to shear effects. It also makes it possible to increase the hydrophilicity of the material and also its disintegration rate.

The carboxyalkyl starches under consideration according to the invention are more particularly potato carboxyalkyl starches.

Thus, the carboxyalkyl starches that may be used according to the present invention are preferably sodium salts of carboxyalkyl starches, in particular a sodium salt of potato carboxymethyl starch, sold especially under the name Primojel by DMV International or Glycolys and Glycolys LV by Roquette.

According to a particular mode, use will be made of the potato carboxymethyl starches sold especially under the name Glycolys by Roquette.

It should be noted that the $C_1$-$C_4$ carboxyalkyl starch particles are present in the compositions according to the invention in a swollen form.

According to one preferred embodiment variant of the invention, these particles are used for the preparation of the compositions according to the invention, in this swollen particulate state. To do so, these particles are advantageously used in the form of an aqueous formulation either prepared beforehand or already commercially available. The gels under consideration according to the invention are advantageously translucent.

Aqueous Phase

A composition according to the invention thus has an aqueous phase which advantageously constitutes its only fluid phase. As specified above, a composition according to the invention is advantageously a single-phase composition. In other words, it is different from an emulsion.

Thus, it comprises an most 0.5% by weight of liquid or solid fatty substance relative to its total weight. The aqueous phase of a composition according to the invention comprises water and at least one lower monoalcohol having from 2 to 5 carbon atoms, in particular represented by at least or even only ethanol.

The aqueous phase (water and optionally the water-miscible solvent) may be present in the composition in a content greater than 60% by weight, ranging from 70% to 95% by weight, preferably from 75% to 90% by weight and better still from 80% to 90% by weight relative to the total weight of said composition.

The weight of the aqueous phase previously considered integrates the weight of the aqueous phase weighted by the weight of all the secondary compounds soluble in this aqueous phase.

Advantageously, a composition according to the invention comprises from 6% to 12.5%, preferably from 8% to 10% of lower monoalcohol and preferably ethanol, relative to the total weight of the composition.

Thus, according to one preferred variant of the invention, the modified crosslinked starch/lower monoalcohol, and preferably ethanol, gelling system is used in a weight ratio at least equal to 0.9 and preferably greater than 1.2, or even greater than 1.5.

Active Agent

A composition of aqueous gel type according to the invention also proves to be advantageous for carrying one or more active agents in particular dedicated to providing the user with a sensory benefit, such as, for example, a freshness, soothing and/or repairing effect.

With regard to consumer expectation for products described as natural, it is advantageous to formulate, in the compositions according to the invention, one or more extracts of plant raw material.

By way of illustration of these active agents, mention may most particularly be made of hydrolates and in particular extracts of Aloe vera.

According to one preferred variant, a composition according to the invention contains at least one hydrolate as active agent.

Hydrolate

In the context of the present invention, the term "hydrolate" is intended to mean an aqueous distillate obtained from a plant raw material by steam distillation.

Steam distillation corresponds to the vaporization, in the presence of steam, of a sparingly water-miscible substance.

The hydrolate according to the invention may be an aqueous distillate, obtained from a whole plant and/or a part of this plant, which remains after the steam distillation, once the separation of the essential oil has been performed. The raw material can be placed in contact with boiling water or steam in an alambic. The steam entrains the essential oil vapour, which is condensed in the condenser and recovered as a liquid phase in a Florentine vase (or essence jar), where the essential oil is separated from the water by settling. The "hydrolate" is thus the aqueous distillate that remains after the steam distillation, once the separation of the essential oil has been performed.

A hydrolate according to the invention can also be referred to as "aromatic water". The hydrolate can also be referred to as a plant water, such as "water from a plant" when it is obtained from a whole plant or from a part thereof, or "floral water" when the hydrolate is obtained from flowers.

The hydrolate according to the invention can be obtained from a plant (or any botanically defined plant raw material), in particular a whole plant and/or a part of a plant. The plant may be in particular a plant, a shrub or flower.

The hydrolate maybe obtained from a whole plant, preferably a plant or of flower, or from a part of this plant chosen from flowers, leaves, stems, seeds, fruits, roots, petals and buds, which can be in various states of dryness (dry, withered, fresh form), and mixtures thereof.

Particularly in the context of the present invention, the hydrolate is a hydrolate of a plant and/or of a part of a plant chosen from the family Rosaceae, preferably genus *Rosa*, the family Asteraceae, preferably genus *Centaurea* and/or genus *Chamaemelum*, the family Lamiaceae, preferably genus *Lavandula*, the family Rutaceae, preferably genus *Citrus*, the family Lamiaceae, preferably genus *Melissa* and/or genus *Mentha*, the family Verbenaceae, preferably genus *Aloysia*, preferably genus *Hordeum*, the family Poaceae, preferably genus *Rosmarinus officinalis* of the family Lamiaceae (or Labiatae), preferably genus *Cupressus* of the family Cupressaceae, preferably genus *Thymus* of the family Lamiaceae (or Labiatae), preferably genus *Salvia* of the family Lamiaceae or Labiate, preferably genus *Nepeta* of the family Lamiaceae, preferably genus *Hamamelis* of the family Hamamelidaceae, preferably genus *Tilia* of the family Tiliaceae, or Malvaceae, subfamily Tilioideae, preferably genus *Satureja* of the family Lamiaceae, and mixtures thereof.

More particularly in the context of the present invention, the hydrolate is a hydrolate of a plant and/or of a part of a plant chosen from *Rosa damascena, Centaurea cyanus, Anthemis nobilis* ou *Chamaemelum nobile, Lavandula angustifolia, Citrus aurantium amara, Melissa officinalis, Mentha piperrita, Lippia citriodora, Hordeum vulgare, Rosmarinus officinalis, Cupressus sempervirens, Thymus vulgaris, Salvia officinalis, Nepeta cataria, Hamamelis virginiana, Tilia cordata, Satureja montana*, and mixtures thereof.

More particularly, the hydrolate present in a composition according to the invention is chosen from a hydrolate obtained from the flowers of *Rosa Damascena*, from the aerial part in bloom of *Centaurea cyanus* L., from the flowers of *Anthemis nobilis* L., from the flowers of *Lavandula angustifolia*, from the flowers of *Citrus de aurantium* L. ssp *Amara*, from the aerial part of *Melissa officinalis* L., from the leaves of *Mentha piperita* L., or from the leaves of *Lippia citriodora* HB & Kuntze, from suckers of *Hordeum vulgare*, from the leaves and branches of *Rosmarinus officinalis*, from the leaves and branches of *Cupressus sempervirens*, from the aerial part in bloom of *Thymus vulgaris*, from the leaves of *Salvia officinalis*, from the aerial part of *Nepeta cataria*, from the leaves of *Hamamelis virginiana*, from the flowers of *Tilia cordata*, from the aerial part in bloom of *Satureja montana* L., and mixtures thereof.

By way of example, the hydrolate of *Rosa damascena*, obtained from the flowers of *Rosa damascena*, or hydrolate of *Rosa Damascena* Miller or hydrolate of rose is in particular available under the trade name Hydrolat De Rose Bio® (containing 100% active material) from Elixens.

By way of example, the hydrolate of *Centaurea cyanus* or hydrolate of *Centaurea cyanus* L. or hydrolate of cornflower is in particular available under the trade name Hydrolat Bleuet Cosm. Bio Dist® (containing 100% active material) from Elixens.

By way of example, the hydrolate of *Anthemis nobilis* or hydrolate of *Anthemis nobilis* L. or hydrolate of chamomile is in particular available under the trade name Hydrolat Camomille Romaine Bio Sica® (containing 100% active material) from Elixens.

By way of example, the hydrolate of *Lavandula angustifolia* or hydrolate of *Lavandula angustifolia* Miller or hydrolate of lavender is in particular available under the trade name Hydrolat De Lavande Bio Sica®) (containing 100% active material) from Elixens.

By way of example, the hydrolate of *Citrus aurantium amara* or hydrolate of *Citrus aurantium* L. ssp *amara* or hydrolate of bitter orange is in particular available under the trade name Hydrolat Fleurs D'Oranger Bio® (containing 100% active material) from Elixens.

By way of example, the hydrolate of *Melissa officinalis* or hydrolate of *Melissa officinalis* L. or hydrolate of lemon balm is in particular available under the trade name Hydrolat Melisse Bio Sica® (containing 100% active material) from Elixens.

By way of example, the hydrolate of *Mentha piperita* or hydrolate of *Mentha piperita* L. or hydrolate of peppermint is in particular available under the trade name Hydrolat Menthe Poivrde Bio Sica® (containing 100% active material) from Elixens.

By way of example, the hydrolate of *Lippia citriodora* or hydrolate of *Lippia citriodora* HB & Kuntze or hydrolate of *Aloysia triphylla* or hydrolate of lemon *verbena* is in particular available under the trade name Hydrolat De Verveine Bio Dist® (containing 100% active material) from Elixens.

By way of example, the hydrolate of *Hordeum vulgare* or hydrolate of suckers of *Hordeum vulgare* or hydrolate of barley is in particular available under the trade name Aquacell Bio Orge PRB from Herbarom.

By way of example, the hydrolate of *Rosmarinus officinalis* or hydrolate of the leaves and branches of *Rosmarinus officinalis* or hydrolate of rosemary is in particular available under the trade name Hydrolat Romarin Bio Sica from Elixens.

By way of example, the hydrolate of *Cupressus sempervirens* or hydrolate of the leaves and branches of *Cupressus sempervirens* or hydrolate of Mediterranean cypress is in particular available under the trade name Hydrolat Cypres Bio Sica from Elixens.

By way of example, the hydrolate of *Thymus vulgaris* or hydrolate of the aerial part in bloom of *Thymus vulgaris* or hydrolate of thyme is in particular available under the trade name Hydrolat Thym Linalol Bio Sica from Elixens.

By way of example, the hydrolate of *Salvia officinalis* or hydrolate of the leaves of *Salvia officinalis* or hydrolate of common sage is in particular available under the trade name Hydrolat Sauge Bio Sica from Elixens.

By way of example, the hydrolate of *Nepeta cataria* or hydrolate of the aerial part of *Nepeta cataria* or hydrolate of catnip is in particular available under the trade name Hydrolat Cataire Citronée Bio Sica from Elixens.

By way of example, the hydrolate of *Hamamelis virginiana* or hydrolate of the leaves of *Hamamelis virginiana* or hydrolate of witch hazel is in particular available under the trade name Eau Florale D'Hamamelis Bio 22.5% from Elixens.

By way of example, the hydrolate of *Tilia cordata* or hydrolate of the flowers of *Tilia cordata* or hydrolate of small leaved lime is in particular available under the trade name Eau Florale De Tilleul Bio 5% from Elixens.

By way of example, the hydrolate of *Satureja montana* or hydrolate of the aerial part in bloom of *Satureja montana* or hydrolate of winter savory is in particular available under the trade name Hydrolat Sarriette Sica Bio from Elixens.

Most particularly suitable for the invention are the hydrates of rose, of cornflower, of lemon balm and of mint.

In the composition according to the invention, the hydrolate may be present in a content of at least 5% by weight, and at most 86% by weight, preferably from 30% to 80% by weight and even more preferentially from 40% to 70% by weight relative to the total weight of the composition.

According to another particular variant, a composition according to the invention may also contain Aloe vera in particular for its repairing and soothing power.

In one particular embodiment, the extract of Aloe vera may be present, in a composition according to the invention, in a content of at least 0.01% by weight, and at most 1% by weight, preferably from 0.05% 0.4% by weight relative to the total weight of the composition.

The material preferentially used is known under the trade reference Aloe Vera Freeze-Dried Powder 200:1 from Mexi Aloe Lab.

Thus, according to one particular embodiment, a composition according to the invention may also comprise at least one extract of Aloe vera and/or a hydrolate of a plant and/or of a part of a plant in particular chosen from *Rosa damascena, Centaurea cyanus, Anthemis nobilis, Lavandula angustifolia, Citrus aurantium amara, Melissa officinalis, Mentha piperrita, Lippia citriodora, Hordeum vulgare, Rosmarinus officinalis, Cupressus sempervirens, Thymus vulgaris, Salvia officinalis, Nepeta cataria, Hamamelis virginiana, Tilia cordata, Satureja montana*, and mixtures thereof.

For a care application in particular, a composition according to the invention may also advantageously comprise at least one moisturizing agent (also known as humectant).

The moisturizer(s) may be present in the composition in a content ranging from 0.1% to 17% by weight, especially from 0.5% to 15% by weight or even from 1% to 10% by weight relative to the total weight of said composition.

As humectants or moisturizing agents, mention may in particular be made of sorbitol, polyhydric alcohols, preferably $C_2$-$C_8$ and even more preferably $C_3$-$C_6$ polyhydric alcohols, such as preferably glycerin, 1,3-propanediol, propylene glycol, 1,3-butylene glycol, pentylene glycol, diglycerin, hexylene glycol, dipropylene glycol, diethylene glycol, and mixtures thereof, glycerol and derivatives thereof, glycol ethers (having in particular from 3 to 16 carbon atoms) such as mono-, di- or tripropylene glycol ($C_1$-$C_4$)alkyl ethers, mono-, di- or triethylene glycol ($C_1$-$C_4$)alkyl ethers, and preferably glycerin.

Mention may be made, as other active agents which can be used in the composition of the invention, for example, of vitamins and mixtures thereof.

The additional and advantageously hydrophilic active agent(s) may be present in the composition according to the invention in a content ranging from 0.001% to 10% by weight, preferably ranging from 0.01% to 5% by weight and preferentially ranging from 0.05% to 1% by weight relative to the total weight of the composition.

The additional active agents for cosmetic treatment of keratin materials, such as the skin, that can be used in the compositions of the invention may in particular be chosen from desquamating agents, antimicrobial agents, soothing agents, antioxidants, astringents, anti-aging agents, firming agents, antiwrinkle agents, and mixtures thereof.

The composition according to the invention comprises at most 0.5% by weight of oil relative to the total weight of the composition.

If present, the oil is chosen from volatile oils such as, in particular, essential oils and lipophilic antioxidants such as tocopherol, or from fragrancing compositions.

According to one particular variant, a composition according to the invention is free of silicone oil.

According to one preferred variant, a composition according to the invention contains at most 5% by weight of surfactants relative to its total weight.

According to another preferred variant, a composition according to the invention comprises at most 0.5% by weight of surfactant relative to its total weight.

According to one particular variant, a composition according to the invention is devoid (free) of surfactant.

By way of surfactants that may be present in the composition, mention may particularly be made of nonionic, anionic, amphoteric or zwitterionic surfactants, promoting the dissolving of fragrance, and the removal of makeup and of impurities.

According to another particular variant, a composition according to the invention may contain one or more foaming surfactants.

As surfactants that are suitable for the invention, mention may in particular be made of (1) nonionic surfactants, such as oxyethylenated oxypropylenated block polymers such as, for example, Poloxamer 184 (CTFA name); fatty esters such as, for example, Emulgin CO 60® (PEG-60 Hydrogenated Castor Oil), $C_{12}$-$C_{24}$ alkanols etherified with 7 to 40 units of ethylene oxide units per fatty molecule, such as, for example, laureth-7, Genapol LA 070 (Clariant International Ltd,) or Steareth-20, for example Genapol HS 200 (Clariant International Ltd).

Mention may also be made of the mixture of glyceryl stearate and of polyethylene glycol 100 EO monostearate, and in particular that comprising a 50/50 mixture, in particular sold under the name Arlacel 165 by Croda;

(2) anionic surfactants, such as alkyl sulfates, alkyl ether sulfates and salts thereof, especially the sodium salts thereof, for instance the mixture of sodium laureth sulfate/magnesium lauryl sulfate/sodium laureth-8 sulfate/magnesium lauryl-8 sulfate sold under the name Texapon ASV® by Henkel; sodium lauryl ether sulfate (70/30 $C_{12}$-$C_{14}$) (2.2 EO) sold in particular under the names Sipon AOS 225® or Texapon N702 Pate® by Henkel, ammonium lauryl ether sulfate (70/30 $C_{12}$-$C_{14}$) (3 EO), in particular that sold under the name Sipon LEA 370® by Henkel; ammonium ($C_{12}$-$C_{14}$) alkyl ether (9 EO) sulfate, in particular that sold under the name Rhodapex AB/20® by Rhodia Chimie.

Mention may also be made of the sulfonates, isethionates, taurates, sulfosuccinates, alkyl sulfoacetates, phosphates and alkyl phosphates.

As sulfonates, mention may for example be made of the α-olefinsulfonates, such as sodium α-olefinsulfonate ($C_{14}$-$C_{16}$), in particular that under the name Bio-Terge AS-40® by Stepan, in particular those sold under the names Witconate AOS Protégé® and Sulframine AOS PH 12® by Witco or in particular that sold under the name Bio-Terge AS-40 CG® by Stepan, secondary sodium olefinsulfonate, in particular that sold under the name Hostapur SAS 30® by Clariant; or linear alkylaryl sulfonates, such as sodium xylene sulfonate, in particular those sold under the names Manrosol SXS30®, Manrosol SXS40® and Manrosol SXS93® by Manro.

As alkyl sulfoacetates, mention may be made of lauryl sulfoacetate, such as, for example, that which is sold as a mixture with sodium methyl-2-sulfolaurate and disodium 2-sulfolaurate under the reference Stepan Mild PCL by Stepan.

Mention may be made, as isethionates, of acylisethionates, such as sodium cocoylisethionate, such as, for example, the product sold under the name Jordapon C1 P® by Jordan.

Taurates that may be mentioned include the sodium salt of palm kernel oil methyltaurate, in particular that sold under the name Hostapon CT Pate® by Clariant; N-acyl N-methyltaurates, for instance sodium N-cocoyl N-methyltaurate, in particular that sold under the name Hostapon LT-SF® by Clariant or sold under the name Nikkol CMT-30-T® by Nikkol, and sodium palmitoyl methyltaurate, in particular that sold under the name Nikkol PMT® by Nikkol.

Mention may be made, as sulfosuccinates, for example, of lauryl (70/30 $C_{12}/C_{14}$) alcohol monosulfosuccinate oxyethylene (3 EO), in particular those sold under the names Setacin 103 Special® and Rewopol SB-FA 30 K 4® by Witco, the disodium salt of a hemisulfosuccinate of $C_{12}$-$C_{14}$ alcohols, in particular that sold under the name Setacin F Special Paste® by Zschimmer Schwarz, disodium oleamidosulfosuccinate oxyethylene (2 EO), in particular that sold under the name Standapol SH 135® by Cognis, oxyethylene (5 EO) lauramide monosulfosuccinate, in particular that sold under the name Lebon A-5000® by Sanyo, the disodium salt of lauryl citrate monosulfosuccinate oxyethylene (10 EO), in particular that sold under the name Rewopol SB CS 50® by Witco, the disodium salt of lauryl alcohol monosulfosuccinate, in particular that sold under the name Rewopol SB F12P® by Witco, or ricinoleic monoethanolamide monosulfosuccinate, in particular that sold under the name Rewoderm S 1333® by Witco.

As phosphates and alkyl phosphates, mention may for example be made of monoalkyl phosphates and dialkyl phosphates, such as lauryl monophosphate, in particular that sold under the name MAP 20® by Kao Chemicals, the potassium salt of dodecylphosphoric acid, a mixture of mono- and diester (predominantly diester), in particular that sold under the name Crafol AP-31® by Cognis, the mixture of octylphosphoric acid monoester and diester, in particular that sold under the name Crafol AP-20® by Cognis, the mixture of ethoxyl (7 mol of EO) 2-butyloctanol phosphoric acid monoester and diester, in particular that sold under the name Isofol 12 7 EO-Phosphate Ester® by Condea, the potassium or triethanolamine salt of mono-($C_{12}$-$C_{13}$)alkyl phosphate, in particular that sold under the references Arlantone MAP 230K-40® and Arlatone MAP 230T-60® by Unigema, potassium lauryl phosphate, in particular that sold under the name Dermalcare MAP XC-99/09® by Rhodia Chimie;

(3) amphoteric or zwitterionic surfactants, such as alkylamido alkylamine derivatives such as N-disodium N-cocoyl-N-carboxymethoxyethyl-N-carboxymethylethylenediamine (CTFA name: Disodium cocoamphodiacetate), in particular that sold as an aqueous saline solution under the name Miranol C2M Conc NP® by Rhodia Chimie; N-sodium N-cocoyl-N-hydroxyethyl-N-carboxymethylethylenediamine (CTFA name: sodium cocamphoacetate) and the mixture of coconut acid ethanolamides (CTFA name: Cocamide DEA).

A composition according to the invention also advantageously contains less than 0.5% by weight, relative to its total weight, of one or more emulsifying polymers.

For the purposes of the invention, the term "emulsifving polymer" is intended to denote a polymer having amphiphilic properties, i.e. having at least one hydrophilic part and at least one hydrophobic part. Hydrophilic groups and hydrophobic groups are well known to those skilled in the art.

For the purposes of the present invention, the term "polymer" is intended to denote a compound comprising at least two repeating units and in particular at least five repeating units.

An emulsifying polymer may especially be a polymer derived from acrylic acid and/or at least one amphiphilic polymer comprising at least one 2-acrylamidomethylpropanesulfonic acid (AMPS) unit.

If present, the emulsifying polymer(s) according to the invention may be chosen from acrylic acid derivatives, and amphiphilic polymers comprising at least one 2-acrylamido-2-methylpropanesulfonic acid (AMPS) unit.

The acrylic acid derivatives comprise:
from 80 mol % to 99 mol % of acrylic acid (AA) units of formula (5) below:

in which $X^+$ is a proton, an alkali metal cation, an alkaline-earth metal cation or the ammonium ion; and
from 1 mol % to 20 mol % and preferably from 1 mol % to 15 mol % of units of formula (6) below:

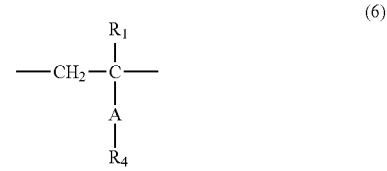

in which $R_1$ denotes a hydrogen atom or a linear or branched $C_1$-$C_6$ alkyl radical (preferably methyl), A denotes an ester or amide group or an oxygen atom and $R_4$ denotes a linear or branched alkyl comprising m carbon atoms with m ranging from 6 to 30 and preferably from 10 to 25.

As acrylic-acid-derived amphiphilic polymers that may be used according to the present invention, mention may be made of:
the non-crosslinked copolymer obtained from (meth) acrylic acid and steareth-methacrylate, sold under the name Aculyn 22® by Röhm & Haas,
the non-crosslinked copolymer obtained from (meth) acrylic acid and laureth-25 methacrylate, sold under the name Aculyn 25® by Röhm & Haas,
the non-crosslinked copolymer obtained from (meth) acrylic acid and beheneth-25 methacrylate, sold under the name Aculyn 28® by Röhm & Haas,
the crosslinked copolymer obtained from (meth)acrylic acid and vinyl neodecanoate, sold under the name Aculyn 38® by Röhm & Haas, the crosslinked copolymer obtained from (meth)acrylic acid and steareth-20 methacrylate, sold under the name Aculyn 88® by Röhm & Haas, crosslinked copolymers of $C_{10}$-$C_{30}$ alkyl acrylate and of (meth)acrylic acid, for instance Pemulen TR1® and TR2® sold by Lubrizol, the crosslinked copolymer of acrylic acid and of vinyl isodecanoate, sold under the name Stabylen 309 by 3V, crosslinked copolymers obtained from (meth)acrylic acid and from $C_{10}$-$C_{30}$ alkyl acrylate, sold under the names Carbopol ETD 2020® and Carbopol 1382® by Lubrizol, the non-crosslinked copolymer obtained from (meth) acrylic acid and steareth-itaconate, sold under the name Structure 2001® by National Starch, the non-crosslinked copolymer obtained from (meth) acrylic acid and ceteth-20 itaconate, sold under the name Structure 3001® by National Starch, the non-crosslinked copolymer obtained from (meth) acrylic acid, aminoacrylate and $C_{10}$-$C_{30}$ alkyl PEG 20 itaconate, sold under the name Structure Plus® by National Starch, and the non-crosslinked copolymer obtained from (meth) acrylic acid, methyl acrylate and ethoxylated alcohol dimethyl meta-isopropenyl benzyl isocyanate, sold under the name Viscophobe DB 1000® by Amerchol.

The acrylic acid-based polymer is in particular a non-crosslinked copolymer obtained from (meth)acrylic acid, methyl acrylate and ethoxylated alcohol dimethyl meta-isopropenyl benzyl isocyanate.

They may in particular be crosslinked copolymers of $C_{10}$-$C_{30}$ alkyl acrylate and of (meth)acrylic acid, for instance Pemulen TR1® and TR2® sold by Noveon.

This emulsifying polymer may also be chosen from amphiphilic polymers comprising at least one 2-acrylamido-2-methylpropanesulfonic acid (AMPS) unit.

The amphiphilic polymers comprising at least one 2-acrylamidomethylpropanesulfonic acid (AMPS) unit that may be used in the present invention, which are also known more simply as "amphiphilic AMPS polymers" hereinbelow, comprise both a hydrophilic part and a hydrophobic part comprising at least one fatty chain:

The fatty chain present in said amphiphilic AMPS polymers according to the invention may preferably comprise from 7 to 30 carbon atoms and more preferentially from 7 to 22 carbon atoms.

The amphiphilic AMPS polymers according to the invention are especially chosen from amphiphilic polymers of at least one acrylamidomethylpropanesulfonic acid (AMPS) monomer and of at least one ethylenically unsaturated comonomer comprising at least one hydrophobic part containing from 7 to 30 carbon atoms and in particular from 7 to 22 carbon atoms or even from 12 to 22 carbon atoms.

The amphiphilic AMPS polymers according to the invention generally have a weight-average molecular weight ranging from 50 000 to 10 000 000 g/mol, in particular from 100 000 to 8 000 000 g/mol and even more particularly from 100 000 to 7 000 000 g/mol.

They may be crosslinked or non-crosslinked.

When the amphiphilic AMPS polymers are crosslinked, the crosslinking agents may be chosen from the polyolefinically unsaturated compounds commonly used for the crosslinking of polymers obtained by free-radical polymerization.

Examples of crosslinking agents that may be mentioned include divinylbenzene, diallyl ether, dipropylene glycol diallyl ether, polyglycol diallyl ethers, triethylene glycol divinyl ether, hydroquinone diallyl ether, ethylene glycol di(meth)acrylate, tetraethylene glycol di(meth)acrylate, trimethylolpropane triacrylate, methylenebis(acrylamide), methylenebis(methacrylamide), triallylamine, triallyl cyanurate, diallyl maleate, tetraallylethylenediamine, tetraallyloxyethane, trimethylolpropane diallyl ether, allyl (meth) acrylate, allylic ethers of alcohols of the sugar series, or other allylic or vinyl ethers of polyfunctional alcohols, and also allylic esters of phosphoric and/or vinylphosphonic acid derivatives, or mixtures of these compounds.

The crosslinking agents may be chosen especially from methylenebis(acrylamide), allyl methacrylate and trimethylolpropane triacrylate (TMPTA).

The degree of crosslinking may range, for example, from 0.01 mol % to mol % and preferably from 0.2 mol % to 2 mol % relative to the polymer.

The amphiphilic AMPS polymers may be chosen especially from random amphiphilic AMPS polymers modified by reaction with a $C_6$-$C_{22}$ n-monoalkylamine or di-n-alkylamine, such as those described in patent application WO 00/31154.

An amphiphilic polymer that is suitable for use in the invention may comprise at least one ethylenically unsaturated hydrophilic monomer chosen, for example, from acrylic acid, methacrylic acid or substituted alkyl derivatives thereof or esters thereof obtained with monoalkylene or polvalkylene glycols, acrylamide, methacrylamide, vinylpyrrolidone, vinylformamide, maleic anhydride, itaconic acid or maleic acid, or mixtures thereof.

An amphiphilic polymer according to the invention may comprise at least one ethylenically unsaturated hydrophobic comonomer.

An amphiphilic polymer that is suitable for use in the invention may comprise at least one hydrophobic part chosen from saturated or unsaturated linear alkyl radicals, for instance n-octyl, n-decyl, n-hexadecyl, n-dodecyl and oleyl, branched alkyl radicals, for instance isosteric, or cyclic alkyl radicals, for instance cyclododecane or adamantane.

An amphiphilic AMPS polymer may also contain at least one ethylenically unsaturated hydrophobic comonomer comprising, for example:

a fluoro or $C_7$-$C_{18}$ fluoroalkyl radical (for example the group of formula —$(CH_2)_2$—$(CF_2)_9$—$CF_3$), a cholesteryl radical or a cholesterol-based radical (for example cholesteryl hexanoate), a polycyclic aromatic group, for instance naphthalene or pyrene, a silicone, alkylsilicone or alkylfluorosilicone radical.

These copolymers are especially described in document EP-A-750 899, patent U.S. Pat. No. 5,089,578 and in the following publications by Yotaro Morishima: "Self-assembling amphiphilic polyelectrolytes and their nanostructures—Chinese Journal of Polymer Science Vol. 18, No 40, (2000), 323-336"; "Micelle formation of random copolymers of sodium 2-(acrylamido)-2-methylpropanesulfonate and a non-ionic surfactant macromonomer in water as studied by fluorescence and dynamic light scattering—Macromolecules 2000, Vol. 33, No 10-3694-3704"; "Solution properties of micelle networks formed by non-ionic moieties covalently bound to a polyelectrolyte: salt effects on rheological behavior—Langmuir, 2000, Vol. 16, No 12, 5324-5332"; and "Stimuli responsive amphiphilic copolymers of sodium 2-(acrylamido)-2-methylpropanesulfonate and associative macromonomers—Polym. Preprint, Div. Polym. Chem. 1999, 40(2), 220-221".

They are also described in documents EP 1 069 142, WO 02/44224, WO 02/44225, WO 02/44227, WO 02/44229, WO 02/44230, WO 02/44231, WO 02/44267, WO 02/44268, WO 02/44269, WO 02/44270, WO 02/44271, WO 02/43677, WO 02/43686, WO 02/43687, WO 02/43688 and WO 02/43689, in the name of Clariant.

An ethylenically unsaturated hydrophobic comonomer of the invention may also be chosen from the acrylates or acrylamides of formula (1) below:

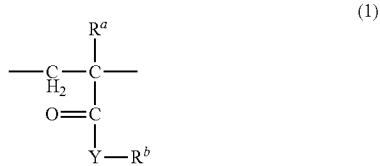

(1)

in which:
R$^a$ denotes a hydrogen atom or a linear or branched C$_1$-C$_6$ alkyl radical, preferably methyl;
Y denotes O or NH;
R$^b$ denotes a hydrophobic radical comprising a fatty chain containing from 7 to 30 carbon atoms, preferably from 7 to 22 and more particularly from 12 to 22 carbon atoms.

The hydrophobic radical R$^b$ is chosen from saturated or unsaturated linear C$_7$-C$_{22}$ alkyl radicals (for example n-octyl, n-decyl, n-hexadecyl, n-dodecyl or oleyl), branched alkyl radicals (for example isostearic) or cyclic alkyl radicals (for example cyclododecane or adamantane); C$_7$-C$_{13}$ alkylperfluoro radicals (for example the group of formula (CH$_2$)$_2$—(CF$_2$)$_9$—CF$_3$); the cholesteryl radical or a cholesterol ester, for instance cholesteryl hexanoate; aromatic polycyclic groups, for instance naphthalene or pyrene.

According to a particular embodiment, the hydrophobic radical R$^b$ may also comprise at least one alkylene oxide unit and preferably a polyoxyalkylene chain.

The polyoxyalkylene chain may preferentially be constituted of ethylene oxide units and/or propylene oxide units and even more particularly be constituted solely of ethylene oxide units.

The number of moles of oxyalkylene units may generally range from 1 to mol, more preferentially from 1 to 25 mol and even more preferentially from 3 to 20 mol.

Among these polymers, mention may be made of:
crosslinked or non-crosslinked, neutralized or non-neutralized copolymers, comprising from 15% to 60% by weight of AMPS units and from 40% to 85% by weight of (C$_8$-C$_{16}$)alkyl(meth)acrylamide or (C$_8$-C$_{16}$)alkyl (meth)acrylate units relative to the polymer, such as those described in patent application EP-A-750 899;
terpolymers comprising from 10 mol % to 90 mol % of acrylamide units, from 0.1 mol % to 10 mol % of AMPS units and from 5 mol % to 80 mol % of n-(C$_6$-C$_{18}$)alkylacrylamide units, relative to the polymer, such as those described in U.S. Pat. No. 5,089,578;
non-crosslinked copolymers of partially or completely neutralized AMPS and of n-dodecyl methacrylate, n-hexadecyl methacrylate or n-octadecyl methacrylate, such as those described in the Morishima articles mentioned above;
crosslinked or non-crosslinked copolymers of partially or completely neutralized AMPS and of n-dodecylmethacrylamide, such as those described in the Morishima articles mentioned above.

Amphiphilic AMPS polymers that may also be mentioned include copolymers of totally neutralized AMPS and of n-dodecyl, n-hexadecyl and/or n-octadecyl methacrylate, and also non-crosslinked and crosslinked copolymers of AMPS and of n-dodecylmethacrylamide.

By way of representation of these amphiphilic AMPS polymers, mention will more particularly been made of the crosslinked or non-crosslinked amphiphilic AMPS copolymers constituted of:
(a) 2-acrylamido-2-methylpropanesulfonic acid (AMPS) units of formula (2) below:

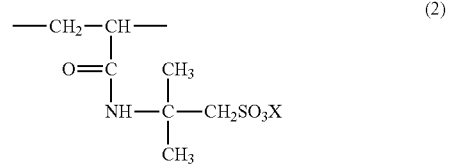

(2)

in which X is a proton, an alkali metal cation, an alkaline-earth metal cation or the ammonium ion;
(b) and units of formula (3) below:

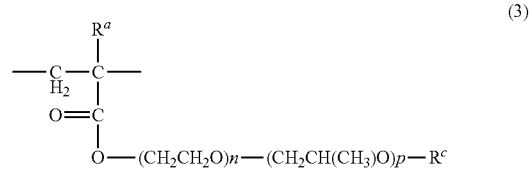

(3)

in which n and p, independently of each other, denote a number of moles and range from 0 to 30, preferably from 1 to 25 and more preferentially from 3 to 20, with the proviso that n+p is less than or equal to 30, preferably less than 25 and better still less than 20; R$^a$ denotes a hydrogen atom or a linear or branched C$_1$-C$_6$ alkyl radical, preferably methyl, and R$^c$ denotes a linear or branched alkyl comprising from 7 to 22 carbon atoms, preferably from 12 to 22 carbon atoms.

In formula (2), the cation X more particularly denotes sodium or ammonium.

Among the monomers of formula (3) that may be mentioned are:
esters of (meth)acrylic acid and of a C$_{10}$-C$_{18}$ fatty alcohol polyoxyethylenated with 8 EO, for instance the product Genapol C-080® sold by Clariant,
esters of (meth)acrylic acid and of a C$_{11}$ fatty oxo alcohol polyoxyethylenated with 8 EO, for instance the product Genapol UD-080® sold by Clariant,
esters of (meth)acrylic acid and of a C$_{12}$-C$_{14}$ fatty alcohol polyoxyethylenated with 7 EO, for instance the product Genapol LA-070® sold by Clariant,
esters of (meth)acrylic acid and of a C$_{12}$-C$_{14}$ fatty alcohol polyoxyethylenated with 11 EO, for instance the product Genapol LA-110® sold by Clariant,
esters of (meth)acrylic acid and of a C$_{16}$-C$_{18}$ fatty alcohol polyoxyethylenated with 8 EO, for instance the product Genapol T-080® sold by Clariant,
esters of (meth)acrylic acid and of a C$_{16}$-C$_{18}$ fatty alcohol polyoxyethylenated with 15 EO, for instance the product Genapol T-150® sold by Clariant,
esters of (meth)acrylic acid and of a C$_{16}$-C$_{18}$ fatty alcohol polyoxyethylenated with 11 EO, for instance the product Genapol T-110® sold by Clariant, esters of (meth)acrylic acid and of a $C_{16}$-$C_{18}$ fatty alcohol polyoxyethylenated with 20 EO, for instance the product Genapol T-200® sold by Clariant, esters of (meth)acrylic acid and of a $C_{16}$-$C_{18}$ fatty alcohol polyoxyethylenated with 25 EO, for instance the product Genapol T-250) sold by Clariant, esters of (meth)acrylic acid and of a $C_{18}$-$C_{22}$ fatty alcohol polyoxyethylenated with 25 EO and/or of a $C_6$-$C_{18}$ fatty isoalcohol polyoxyethylenated with 25 EO.

Most particularly advantageous are:

a) those which are non-crosslinked, for which p=0, n=7 or 25, $R^a$ denotes a methyl and $R^c$ represents a mixture of $C_{12}$-$C_{14}$ or $C_{16}$-$C_{18}$ alkyl, b) those which are crosslinked, for which p=0, n=8 or 25, $R^a$ denotes a methyl and $R^c$ represents a mixture of $C_6$-$C_{18}$ alkyl.

These polymers are described and synthesized in patent application EP 1 069 142.

These particular amphiphilic AMPS polymers may be obtained according to the standard free-radical polymerization processes in the presence of one or more initiators, for instance azobisisobutyronitrile (AIBN), azobisdimethylvaleronitrile, 2,2-azobis[2-amidinopropane] hydrochloride (ABAH), organic peroxides such as dilauryl peroxide, benzoyl peroxide or tert-butyl hydroperoxide, mineral peroxide compounds such as potassium persulfate or ammonium persulfate, or $H_2O_2$ optionally in the presence of reducing agents.

These amphiphilic AMPS polymers may be obtained especially by free-radical polymerization, in tert-butanol medium, in which they precipitate. By using precipitation polymerization in tert-butanol, it is possible to obtain a size distribution of the polymer particles that is particularly favorable for its uses.

The reaction may be performed at a temperature of between 0 and 150° C. and preferably between 10 and 100° C., either at atmospheric pressure or under reduced pressure.

It may also be performed under inert atmosphere and preferably under nitrogen.

These amphiphilic AMPS polymers may be partially or totally neutralized with a mineral base such as sodium hydroxide, potassium hydroxide, aqueous ammonia or an organic base such as monoethanolamine, diethanolamine, triethanolamine, an aminomethylpropanediol, N-methylglucamine, basic amino acids, for instance arginine and lysine, and mixtures of these compounds. They may especially be totally or almost totally neutralized, i.e. at least 80% neutralized.

The molar % concentration of the units of formula (2) and of the units of formula (3) in the amphiphilic AMPS polymers can range between 0.1 mol % and 99.9 mol %.

The distribution of the monomers in the amphiphilic AMPS polymers according to the invention may be, for example, alternate, block (including multiblock) or random.

By way of indication, mention may be made especially of the copolymer of AMPS and of ethoxylated $C_{12}$-$C_{14}$ alcohol methacrylate (non-crosslinked copolymer obtained from Genapol LA-070 and from AMPS) (CTFA name: Ammonium Acryloyldimethyltaurate/Laureth-7 methacrylate copolymer) sold under the name Aristoflex LNC® by Clariant, the copolymer of AMPS and of ethoxylated stearyl methacrylate (25 EO) (copolymer crosslinked with trimethylolpropane triacrylate, obtained from Genapol T-250 and from AMPS) (CTFA name: Ammonium Acryloyldimethyltaurate/Steareth-25 Methacrylate Crosspolymer) sold under the name Aristoflex HMS® by Clariant, Aristoflex SNC (80/20 copolymer of AMPS/ethoxylated (8 mol EO) $C_{16}$/$C_{18}$ alcohol methacrylate; CTFA name: Ammonium Acrylovldimethyltaurate/Steareth-8 methacrylate copolymer) and Aristoflex HMB® (copolymer of AMPS/ethoxylated (25 EO) behenyl methacrylate, crosslinked with trimethylolpropane triacrylate (TMPTA)).

Finally, according to another preferred embodiment, a composition according to the invention is free of emulsifying hydrocolloids like natural gums and in particular xanthan gum, carrageenan (lambda, iota, kappa), sclerotium gum, microcrystalline cellulose, cellulose gum, pectin, acacia Senegal gum and *Caesalpinia spinosa* gum.

Secondary Ingredients

A composition according to the invention may also contain one or more colorants, of water-soluble pigment or dye type.

The composition according to the invention may also comprise adjuvants that are common in the cosmetics and dermatology fields, such as antioxidants, fragrances, conditioning agents and preservatives. The amounts of these various adjuvants are those conventionally used in the fields under consideration, and for example from 0.01% to 20% of the total weight of the composition.

Needless to say, those skilled in the art will take care to select the optional compound(s) to be added to the compositions according to the invention and also the concentration thereof, such that the advantageous properties intrinsically associated with the compositions in accordance with the invention are not, or are not substantially, adversely affected by the envisioned addition.

The invention is also directed toward a process for preparing a composition, comprising at least the steps consisting in providing a homogeneous aqueous dispersion of at least 7.5% by dry weight of at least one modified crosslinked $C_1$-$C_4$ carboxyalkyl starch relative to the total weight of the aqueous dispersion and bringing this aqueous dispersion into contact with at least one $C_2$-$C_5$ lower alcohol.

The homogeneous aqueous formulation of crosslinked $C_1$-$C_4$ carboxyalkyl starch can be pre-prepared by mechanical stirring of the non-hydrated form of crosslinked $C_1$-$C_4$ carboxyalkyl starch in water and by heating the whole mixture to a temperature of from 50 to 55° C.

The composition according to the invention may be a care composition, in particular may be a skin care product such as a lotion, a skin care base, a care gel (day, night, anti-wrinkle care), a makeup removal base; a cleansing or makeup removal composition for the skin and advantageously a cleansing or care mask.

More particularly, the composition according to the invention is intended to be suitable to be administered topically, that is to say by application to the surface of the keratin material under consideration, such as the skin under consideration.

According to the invention, the term "keratin materials" is intended to mean the skin, of the body, face and/or area around the eyes, the lips, the nails, the mucous membranes, the eyelashes, the eyebrows, bodily hair, the scalp and/or the hair, or any other area of bodily skin. More particularly, the keratin materials according to the invention are the scalp, the hair and/or the skin.

Preferably, the keratin material according to the invention is the skin.

The term "skin" is intended to mean all of the skin of the body, and preferably the skin of the face, neckline, neck, arms and forearms, or even more preferably still the skin of the face, in particular of the forehead, nose, cheeks, chin and area around the eyes.

A subject of the present invention is also the cosmetic use of a composition according to the invention for caring, cleansing and/or removing makeup from keratin materials, in particular the skin.

A subject of the present invention is also a process for cosmetically treating keratin materials, in which a composition as defined above is applied to said keratin material(s).

The cosmetic treatment process is more particularly a cosmetic treatment process for caring, cleansing and/or removing makeup from keratin materials, and preferably the skin.

The examples that follow illustrate the invention, and are given purely as nonlimiting illustrations.

Throughout the text hereinbelow, the percentages are given on a weight basis, unless otherwise mentioned.

The expressions "between . . . and . . . " and "ranging from . . . to . . . ", "at least of . . . " or "at most of" should be understood as being limits inclusive, unless otherwise specified.

The examples and figures that follow are provided as illustrations which do not limit the field of the invention.

FIGURE

MATERIALS AND METHODS

Stability Test:

It makes it possible to verify the stability under conditions making it possible to simulate accelerated aging. It is carried out in centrifugation mode at D1 after production.

After centrifugation, the presence or absence of any release or decanting phenomenon is controlled by direct observation.

The centrifuge used is a Firlabo brand/Model SW 9 centrifuge and the working specificities thereof are the following:

Time: 60 min
Temperature: AT
Tube: Round-bottomed glass tube
Weight: 37 g tube & liquor included
Viscosity Measurement The viscosities in Pas are determined by oscillation and obtained at 25° C. using a Haake Mars II imposed-stress rheometer equipped with a plate-cone measuring body (diameter 60 mm, 1 degree and in sanded titanium, 25° C.). For each measurement, the sample is carefully put in place and the gap is set at 0.052 mm.

The viscosities in DU are characterized by means of a rheometer (Rheomat RM200 from Lamy) using spindle 4. The viscosity is taken at D1, then T2M at ambient temperature and at 45° C. The measurement is thermostated at 25° C.

Freshness Measurement Test

It is carried out by in vitro evaluation of the potential generation of an extemporaneous fresh effect due to an endothermic reaction in solution. This effect is assessed by measuring the temperature at various time intervals.

Figure 2:
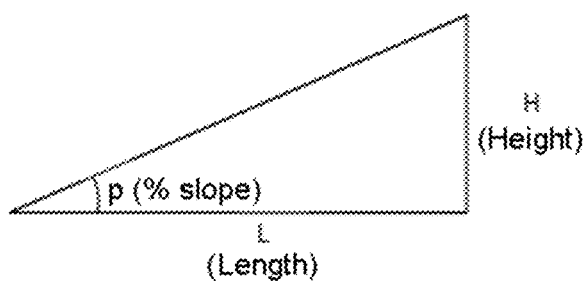
FIG. 2 illustrates the freshness effect and the persistence thereof are demonstrated by the slope calculated as a percentage (%) defined by the height divided by the length between 2 points at To and T10 min (corresponding to the leave-on time of the mask).

The materials and parameters required are as follows:
Mixer with a stirring speed of 3500 r/3 min
Specific pot 60 g
Amount of the formulation to be characterized at 45 g
T° taken at T0 min-T5 min-T10 min-T5 min-T20 min
Thermometer: Brand Multi Thermometer Model 900 AT The freshness effect and the persistence thereof are demonstrated by the slope calculated as a percentage (%) defined by the height divided by the length between 2 points at To and T10 min (corresponding to the leave-on time of the mask) (see FIG. 2).

$$P = H/L \times 100$$

The greater the slope, the greater the validation of the perceived and persistent freshness effect, in particular during the first 10 minutes (which corresponds to the leave-on time of the mask).

In Vivo Freshness and Sensory Evaluation Test

This type of evaluation is carried out on a panel of 5 Caucasian women, between 20 and 35 years old, who are regular users of masks in gel form.

The test aims to evaluate the use qualities and the cosmetic properties, in particular the freshness during the application and the leave-on time, the rinsability and also the perceived effectiveness in terms of softness and plumped skin.

The tests are carried out at home on 3 formulations. Test of each product for 3 days by replacing the usual face mask (one application per day over the 3 days+1 day pause before beginning the test on the next product).

Pilling Evaluation Test:

This evaluation is carried out on a panel of 10 men working in the sector of the formulation of cosmetic galenical forms.

The protocol thereof consists in:
performing a single application of 50 µml of product to the forearm at the center of a 5 cm by 3 cm rectangle, and
carrying out 15 revolutions with 2 fingers/waiting for 15 s/again carrying out 15 revolutions/leave-on time of 2 min/carrying out 5 energetic revolutions, without wiping the fingers throughout the duration of the test.

Grading for the absence or presence of pills: 1 to 5
1=Absence of pills
3=Intermediate presence of pills
5=Many pills
Grading for ease of pilling:
Easy—Moderately Easy—Difficult

EXAMPLES

Example 1

Compositions According to the Invention

| PHASE | Chemical name | Composition 1 (% by weight) | Composition 2 (% by weight) |
|---|---|---|---|
| A1 | MICROBIOLOGICALLY CLEAN DEIONIZED WATER | Qs 100 | Qs 100 |
| A1 | GLYCERIN OF PLANT (PALM) ORIGIN (Glycerin 4810 from OLEON) | 5 | 5 |
| A1 | 1,3-PROPANEDIOL (Zemea Propanediol from DuPont Tate and Lyle Bio Products) | 5 | 5 |

-continued

| PHASE | Chemical name | Composition 1 (% by weight) | Composition 2 (% by weight) |
|---|---|---|---|
| A2 | PURIFIED POWDERED ALOE EXUDATE (Aloe Vera Freeze Dried Powder Organic 200:1 from Mexi Aloe Lab) | 0.45 | 0.36 |
| B | CROSSLINKED SODIUM CARBOXYMETHYL STARCH (POTATO) (Glycolys from Roquette) | 10 | 10 |
| C | DENATURED ETHYL ALCOHOL 96° (Ethanol S96 Denature Bitrex/Tertio from France Alcools) | 8 | 8 |
| C | SALICYLIC ACID POWDER (Salicylic Acid USP from Alta Laboratories) | 0.2 | 0.2 |
| C | FRAGRANCE | 0.04 | 0 |
| D | CITRIC ACID MONOHYDRATE | | 0.16 |
| | Measurement of viscosity in DU | 107 | — |
| | Measurement of viscosity in Pa | 7600 | — |
| | Measurement of viscosity in Pa · s | 250 | — |

Compositions 1 and 2 were prepared as follows.

The constituents of phase A1 are homogenized with blade and scraper stirring and the whole mixture is heated to a temperature of 50° C. to 55° C. The constituents B, premixed beforehand, are added to this heated mixture. The whole mixture is maintained under blade and scraper stirring until emulsion, heating and total hydration of the carboxymethyl starch.

Once this level of hydration has been achieved, the mixture is cooled to a temperature of 22° C. to 23° C. with blade and scraper stirring.

At 22° C., the constituent elements of phase C are added with stirring, followed by the citric acid (D). The stirring is maintained for 5 minutes.

The gels thus obtained are flexible and homogeneous with a translucent and slightly "grained" and matte appearance.

Their texture is suitable for a fresh and easy to measure out mask application.

On application, composition 1 was characterized, according to the tests described above in the materials and methods chapter, as having glidance, having good adhesion, being not very tacky, being easy to apply and providing an immediate freshness effect. For the finished skin, it was characterized as being soft and non-tacky. More specifically, during application, the fingers glide on the product and thus allow a homogeneous application to the skin.

Composition 2 applied to the skin was removed after a leave-on time of 5 to 10 minutes with an application in a thick layer, by circular massaging movements, thereby allowing gentle exfoliation by pilling before rinsing with water. The degree of pilling was evaluated as highly pilling and very easy to pill throughout the evaluation with a final rinsing. The product is thus easy to rinse off and easy to pill.

Example 2

The formulations described in detail in table 1 hereinafter were prepared and their respective parameters P, characteristic of the associated freshness effect, were determined according to the test specified above in the materials and methods chapter.

TABLE 1

| Formulation | Alcohol | Modified starch (Glycolis) | Water | P Slope (%) |
|---|---|---|---|---|
| 1 | 0 | 0 | qs 100 | 5 |
| 2 | 5% | 0 | qs 100 | 9 |
| 3 | 8% | 0 | qs 100 | 12 |
| 4 | 10% | 0 | qs 100 | 13 |
| 5 | 15% | 0 | qs 100 | 16 |
| 6 | 0 | 10% | qs 100 | 35 |
| 7 | 8% | 7.5% | qs 100 | 15 |
| 8 | 8% | 10% | qs 100 | 47 |
| 9 | 8% | 12.5% | qs 100 | 35 |

Figure 1:
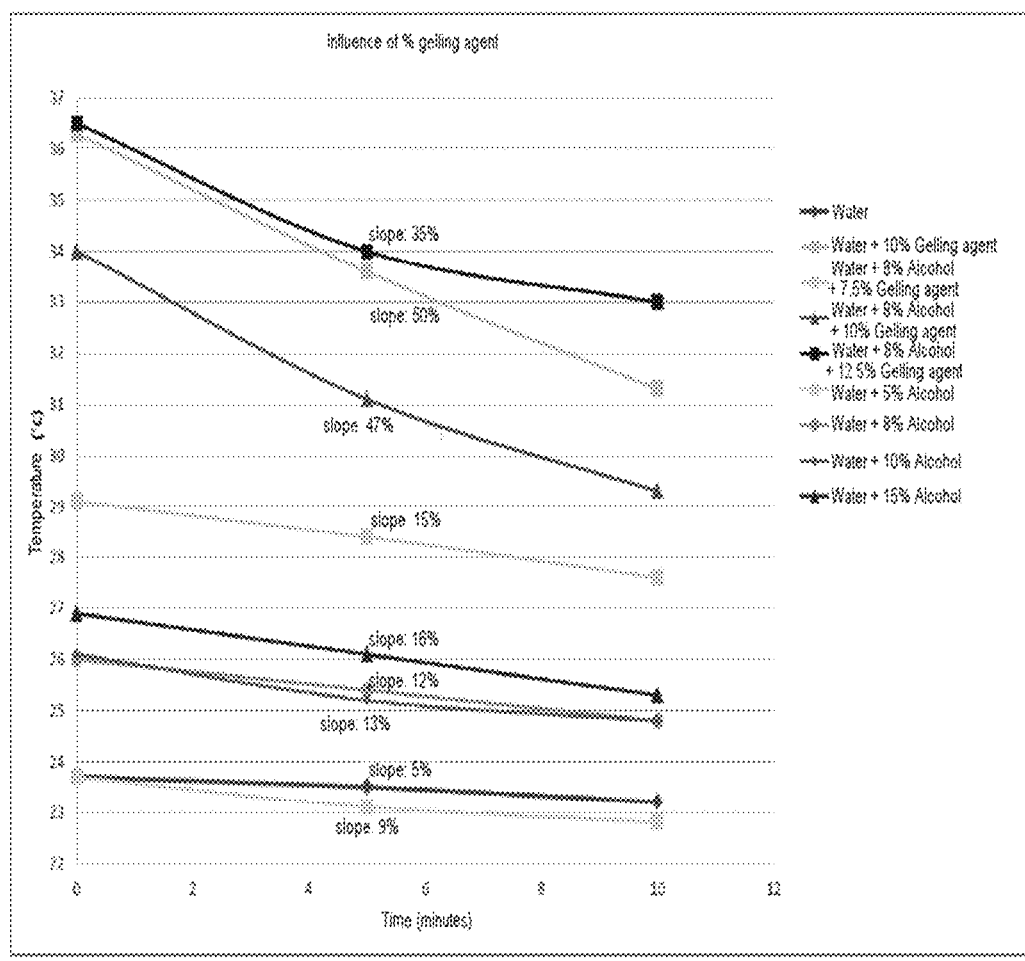
FIG. 1 illustrates the freshness effect characterized in Example 2.

FIG. 1 also gives these results.

As specified in the protocol, the higher the value P, representative of the slope, the greater the validation of the perceived and persistent freshness effect.

It emerges that the most significant gains in freshness effect and in persistence at 10 min (leave-on time of the mask) are noted in the presence of the gelling agent alone or at gelling agent contents including from 7.5% to 12.5% combined with ethanol. These results also make it possible to note the very low impact of ethanol or of water on the providing of this effect.

Example 3

Influence of the Variations in Amount of Starch and of Alcohol on the Cosmetic Qualities of the Gel-Type Compositions Compositions 3 to 5 according to the invention and control compositions A to D were prepared according to the process described in example 1.

Table 2 below gives the detailed composition of these compositions and their characterization.

TABLE 2

| | COMPOSITIONS ACCORDING TO THE INVENTION | | | CONTROL COMPOSITIONS | | | |
|---|---|---|---|---|---|---|---|
| Chemical name | NO. 3 | NO. 4 | NO. 5 | CONTROL A | CONTROL B | CONTROL C | CONTROL D |
| MICROBIOLOGICALLY CLEAN DEIONIZED WATER | Qs 100 | Qs 100 | Qs 100 | Qs 100 | Qs 100 | Qs 100 | Qs 100 |
| GLYCEROL | 5 | 5 | 5 | 5 | 5 | 5 | 5 |
| 1,3-PROPANEDIOL | 5 | 5 | 5 | 5 | 5 | 5 | 5 |
| PURIFIED POWDERED ALOE EXUDATE | 0.36 | 0.36 | 0.36 | 0.36 | 0.36 | 0.36 | 0.36 |

TABLE 2-continued

| | COMPOSITIONS ACCORDING TO THE INVENTION | | | CONTROL COMPOSITIONS | | | |
|---|---|---|---|---|---|---|---|
| Chemical name | NO. 3 | NO. 4 | NO. 5 | CONTROL A | CONTROL B | CONTROL C | CONTROL D |
| CROSSLINKED SODIUM CARBOXYMETHYL STARCH (POTATO) | 10 | 10 | 12 | 10 | 10 | 7.5 | 15 |
| DENATURED ETHYL ALCOHOL 96° | 8 | 10 | 8 | 0 | 5 | 8 | 8 |
| SALICYLIC ACID POWDER | 0.2 | 0.2 | 0.2 | 0.2 | 0.2 | 0.2 | 0.2 |
| CITRIC ACID MONOHYDRATE | 0.26 | 0.41 | 0.32 | 0.24 | 0.26 | 0.16 | 0.16 |
| PROPERTIES TESTED | | | | | | | |
| Visual characterization at 1 day | Homogeneous flexible matte gel, slight translucent "grained" effect | Homogeneous flexible matte gel, slight translucent "grained" effect | Homogeneous flexible matte gel, slight translucent "grained" effect | Homogeneous flexible matte gel, slight translucent "grained" effect | Homogeneous flexible matte gel, slight translucent "grained" effect | Gel less satisfactory | |
| Characterization of the stability by centrifugation at 1 day | suitable | suitable | suitable | suitable | suitable | Unacceptable | suitable |
| Viscosity at 1 day | 107 DU | 56.6 DU | 147 DU | 122 DU | 74.2 DU | 10.9 DU | 175 DU |
| Grading of Pilling Absence or Presence | 5 | 5 | 4 | 4.5 | 4 | Not evaluated | Not evaluated |
| Grading of ease of pilling | Easy | Easy | Easy | Medium | Medium | Not evaluated | Not evaluated |
| Freshness Effect | Validated | Validated | Validated | Not evaluated | Not evaluated | Not evaluated | Not evaluated |

The analysis of the results reveals that the sodium carboxymethyl starch must be present in an amount greater than 7.5% by dry weight of active material in order to obtain a stabilized gelled composition having the expected characteristics in terms of sensoriality (freshness, etc.) and pilling.

Example 4

Composition According to the Invention Incorporating a Hydrolate

| | Chemical name | % by weight |
|---|---|---|
| A1 | MICROBIOLOGICALLY CLEAN DEIONIZED WATER | Qs 100 |
| | STABILIZED ROSE HYDROLATE (FLOWERS) (Hydrolat De Rose Bio ® (containing 100% active material) from Elixens) | 50 |
| A1 | GLYCERIN OF PLANT (PALM) ORIGIN (Glycerin 4810 from Oleon) | 5 |
| A1 | 1,3-PROPANEDIOL (Zemea Propanediol from DuPont Tate and Lyle Bio Products) | 5 |
| A2 | PURIFIED POWDERED ALOE EXUDATE (Aloe Vera Freeze Dried Powder Organic 200:1 from Mexi Aloe Lab) | 0.45 |
| B | CROSSLINKED SODIUM CARBOXYMETHYL STARCH (POTATO) (Glycolys from Roquette) | 10 |
| C | DENATURED ETHYL ALCOHOL 96° (Ethanol S96 Denature Bitrex/Tertio from France Alcools) | 8 |
| C | SALICYLIC ACID POWDER (Salicylic Acid USP from Alta Laboratories) | 0.2 |
| C | FRAGRANCE | 0.04 |

This composition is prepared according to the protocol described in Example 1.

The gel thus obtained is flexible and homogeneous and has a translucent, matte appearance.

Its texture is suitable for a fresh and easy to measure out mask application.

On application, it is characterized as having glidance, adhering well, being not very tacky, being easy to apply and providing an immediate freshness effect. For the finished skin, it was characterized as being soft and non-tacky.

Its degree of pilling was evaluated, after a leave-on time of 5 to 10 minutes with application in a thick layer, as highly pilling and very easy to pill throughout the evaluation with a final rinsing.

The invention claimed is:

1. Composition of aqueous gel type comprising from 7.5% to 13.5% by dry weight of at least one modified crosslinked $C_1$-$C_4$ carboxyalkyl starch relative to its total weight and at least one $C_2$-$C_5$ monoalcohol.

2. Composition according to claim 1, wherein it is a single-phase composition.

3. Composition according to claim 1, in which said $C_1$-$C_4$ carboxyalkyl starch has a degree of substitution of carboxyalkyl units ranging from 0.1 to 1.

4. Composition according to claim 1, in which said $C_1$-$C_4$ carboxyalkyl starch is a carboxymethyl starch formed from units of formula:

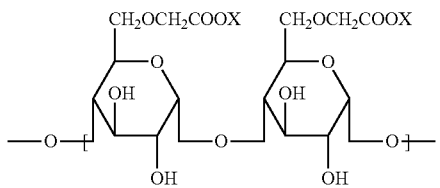

in which X, covalently or non-covalently bonded to the carboxylic unit, denotes a hydrogen atom, an alkali metal or alkaline-earth metal, a quaternary ammonium or an organic amine.

5. Composition according to claim 1, in which said $C_1$-$C_4$ carboxyalkyl starch is a crosslinked sodium carboxymethyl starch.

6. Composition according to claim 1, comprising from 7.5% to 12% by dry weight of modified crosslinked $C_1$-$C_4$ carboxyalkyl starch relative to its total weight.

7. Composition according to claim 1, comprising at least ethanol as lower monoalcohol.

8. Composition according to claim 1, comprising from 6% to 12.5% by weight of lower monoalcohol relative to its total weight.

9. Composition according to claim 1, in which the modified crosslinked starch and the lower monoalcohol are used in a modified crosslinked starch/lower monoalcohol weight ratio at least equal to 0.9.

10. Composition according to claim 1, comprising at least one extract of aloe vera and/or a hydrolate of a plant and/or of a part of a plant.

11. Composition according to claim 1, comprising at most 0.5% by weight of surfactant relative to its total weight.

12. Composition according to claim 1, comprising at most 0.5% by weight of liquid or solid fatty substance relative to its total weight.

13. Composition according to claim 1, wherein it is in the form of a skin cleansing composition.

14. Process for preparing a composition according to claim 1, comprising at least the steps consisting in:
providing a homogeneous aqueous dispersion of at least 7.5% by dry weight of at least one modified crosslinked $C_1$-$C_4$ carboxyalkyl starch relative to the total weight of the aqueous dispersion, and
bringing this aqueous dispersion into contact with at least one $C_2$-$C_5$ lower monoalcohol.

15. Method for caring, cleansing and/or removing makeup from keratin materials comprising at least a step of applying a composition according to claim 1, for caring, cleansing and/or removing makeup from at the surface of keratin materials.

16. Process for cosmetic treatment of keratin materials, in which a composition as defined in claim 1 is applied to said keratin materials.

17. Cosmetic process for cleansing a keratin material comprising at least the steps consisting in:
forming, at the surface of said keratin material to be treated, a mask from a composition according to claim 1, and
removing said mask by rinsing and/or by pilling.

* * * * *